US00PP10401P

United States Patent [19]

Morren

[11] Patent Number: Plant 10,401

[45] Date of Patent: May 19, 1998

[54] VARIETY OF APPLE TREE NAMED JONAGORED SUPRA

[75] Inventor: Jos Morren, Halen, Belgium

[73] Assignee: Jomobel NV, Belgium

[21] Appl. No.: 787,620

[22] Filed: Jan. 23, 1997

[30] Foreign Application Priority Data

Jan. 25, 1996 [EP] European Pat. Off. ..... 200/96

[51] Int. Cl.[6] ..... A01H 5/00

[52] U.S. Cl. ..... Plt./34.1

[58] Field of Search ..... Plt./34.1

*Primary Examiner*—James R. Feyrer
*Attorney, Agent, or Firm*—Olson & Olson

[57] ABSTRACT

A new and distinctive variety of apple *Malus domestica*, tree named Jonagored Supra, a sport mutation of the apple variety Jonagored, uniquely characterized from its parent variety by the rounder form of its fruit; its slightly softer red-colored, approximately 90% solid blush having scarcely visible, very fine red stripes in it and approximately 10% of its surface is striped; by the earlier ripening and picking dates of its fruit; by the tree's distinctly weaker growth habit, the very dark brown to greyed-purple color of its wood; more pubescence and a lower amont of lenticels; and by the irregular margin of its leaves which is generally serrate but some are also biserrate and serrate-biserrate. Extended observation has further indicated that the Jonagored Supra is virus free, and is an improvement on the Jonagored variety with respect to its growth habit, color and productivity.

4 Drawing Sheets

This application claims the benefit of the right of priority accorded under the International Convention for the Protection of New Varieties of Plants (UPOV Convention) of European Union Community Plant Variety Rights Application NR 0200/96 filed 25 Jan. 1996.

BACKGROUND OF THE INVENTION

This invention relates to a new and distinct variety of apple tree named Jonagored Supra.

The new apple variety was discovered in a cultivated Jonagored apple orchard located at Halen, Belgium as a sport mutation of the Jonagored apple tree, U.S. Pat. Plant No. 5,937. It was noted that one tree in the orchard was unique and different in appearance from the entire block of Jonagored trees. This whole tree mutation was propagated by means of a probably spontaneous mutated eye that was taken as budwood. Its fruit coloring started with a green-orange-red color about 10th August, while the coloring of the cultivated fruit of Jonagored started later with a striped-brown-red color.

Observation of the mutated tree over a period of five weeks indicated that the condition of the fruit remained stable although its color gradually became dark-red with scarcely visible very fine red stripes in it. In comparision with the parent variety, the Jonagored Supra is already, picking-ripe and completely red, eight days before the fruit of the parent variety. Cuttings were made from the sport mutation and the new variety was reproduced by grafting. Extending observation in Halen, Belgium has shown that the unique and distinguishing characteristics of the mutated tree and its fruit have remained consistent through its third generation descendants. Both the descendants and the original mutated tree continue to share the very same characteristics and fruit color described. Extended observation has also indicated that the Jonagored Supra is virus free and it is an improvement of the Jonagored variety with respect to its growth habit, color and productivity.

Various differences between the parent Jonagored apple variety and the new Jonagored Supra apple variety are itemized in the following comparison table. With respect to the following dates of the Jonagored parent variety, the United States Plant Patent and the table of characteristics from the testing station in Brogdale, England was used.

TABLE A

| JONAGORED | JONAGORED SUPRA |
|---|---|
| Tree: | |
| stronger growth | weaker growth although it is virus free although the Jonagored is very productive, this variety is even more productive |
| Wood: | |
| more and bigger lenticels | less lenticels; generally round points more pubescence darker brown/purple color |
| Leaves: margin: | |
| serrate | generally serrate (82%) biserrate (9%) serrate-biserrate (9%) |
| Petiole + veins: | |
| purple-red colored | green and light purple-red colored against the stem petioles are longer |
| Dormant fruit bud: | |
| conical | conical-ovoid: |
| Fruit: | |
| form:round conical crowning at distal end:present color: 50% blush 50% stripes more hard red/ red coloring +75% color intention | form:round crowning at distal end: weak color: 90% blush 10% stripes slightly softer red/red coloring 90% to 95% color intention coloring and ripening is 8 days earlier than Jonagored |
| Fruit in cross-section: | |
| cells are open | cells are more open |

THE DRAWINGS

The accompanying drawings illustrate my new Jonagored Supra apple tree and the characteristics of its fruit taken at the time of fruit ripening for keeping.

DESCRIPTION OF THE NEW VARIETY

Figure 1:
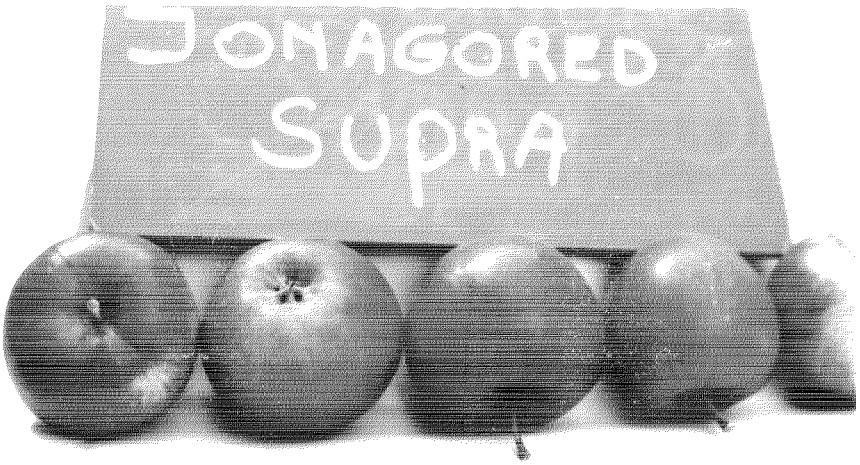
FIG. 1 illustrates the shape of the apple from every side.
Figure 2:
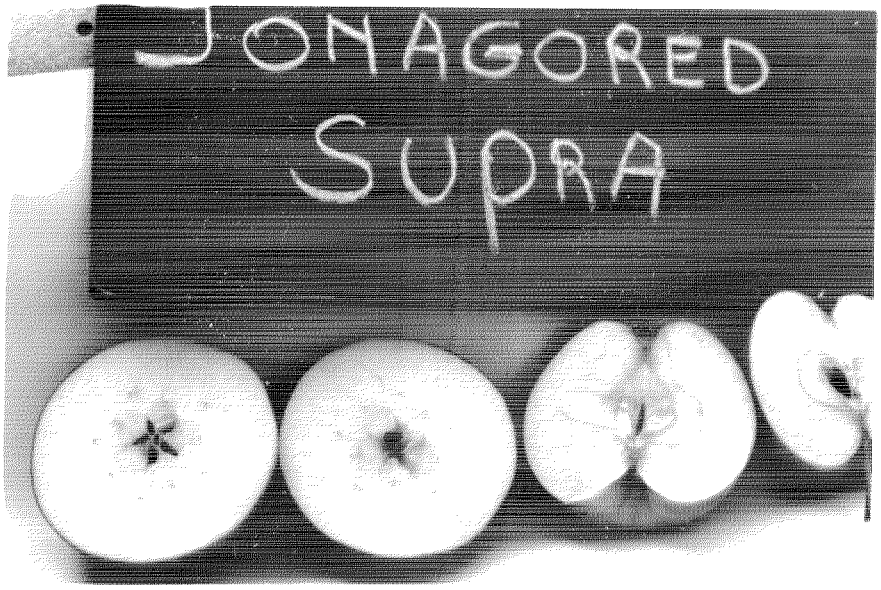
FIG. 2 is a view illustrating longitudinal and transverse sections taken through the fruit of the Jonagored Supra variety.
Figure 3:
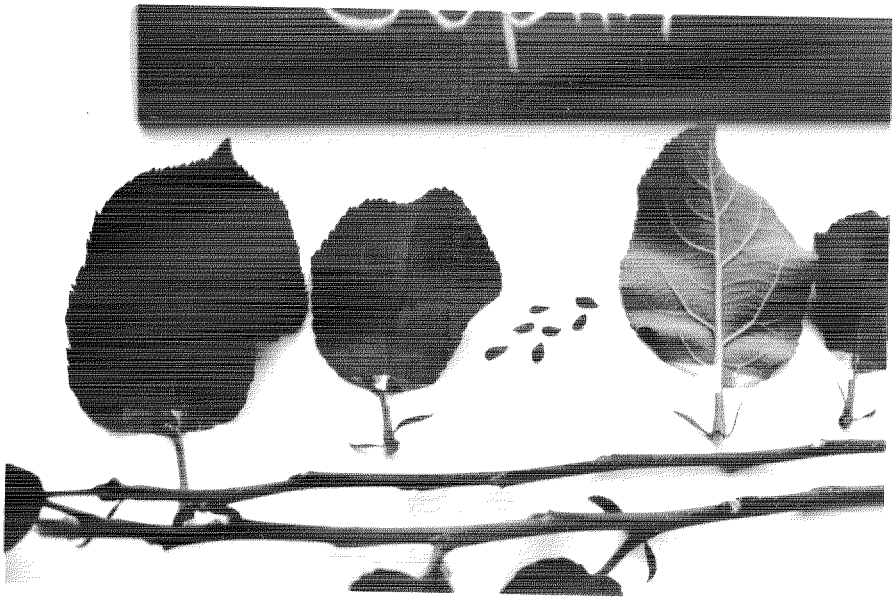
FIG. 3 is a view of the leaves and branches of the new apple tree, along with the seeds of its fruit.
Figure 4:
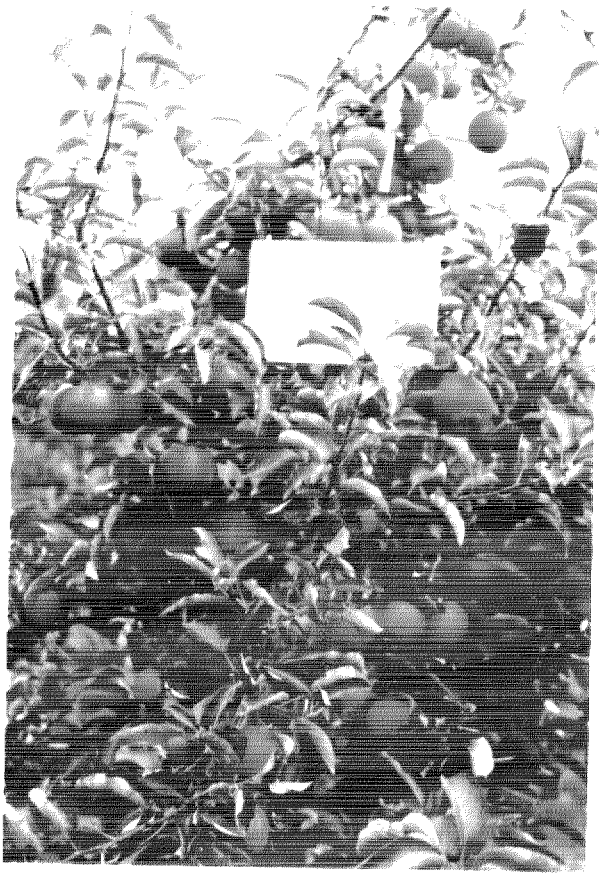
FIG. 4 illustrates the over all appearance and growth habit of the Jonagored Supra apple tree.
Figure 5:
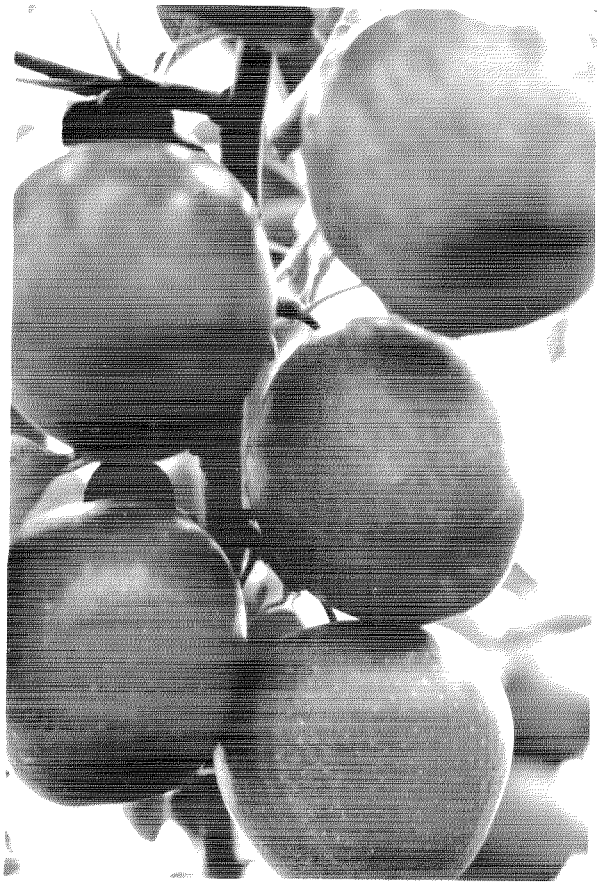
FIG. 5 is a closer view of a portion of the Jonagored Supra apple tree shown in FIG. 4.

The following is a detailed description of the new apple tree variety Jonagored Supra as grown and observed at Halen, Belgium. Color references are made to The Royal Horticultural Colour Chart of London in association with the Flower Council of Leiden — Holland (1986) except where general color terms of ordinary dictionary significance are used.

Parentage: A sport mutation of the apple tree variety Jonagored.

Propagation: Asexually by budding and grafting.

The Tree

Form: Medium size.

Habit of growth: Generally rapid, very productive, regular bearer.

Vigor (based on height and spread): Weak-medium.

Trunk: Medium stocky, smooth, medium strong.

Branches: Drooping.

Density of head: Medium.

Predominance of bearing: On spurs (also tips).

Dormant one-year old shoot (on October 14th):

*Thickness.*—Medium.

*Pubescence.*—Moderate; round about the shoot.

*Internode.*—From 0.04 to 4.08 cm (average of 2.31 cm).

*Number of lenticels.*—Few through present.

*Size of lenticels.*—Small; maximum 1.5 mm long; generally round points.

*Wood bud.*—Pubescence (on upper half of shoot): Moderate.

*Form.*—Relatively straight.

*Color of the wood.*—Upper side: with pubescence dark-brown, darker than greyed group 201A; without pubescence between brown group 200A and greyed-purple group 187A; underside: with pubescence greyed-green group 197A; without pubescence a bit darker than yellow-green group 152A (more brownish).

Dormant fruit buds (on October 14th):

*Shape.*—Conical-ovoid.

*Apex.*—Moderately pointed.

*Pubescence.*—Moderate.

*Size.*—Medium.

*Length.*—From 4.61 to 7.54 mm.

*Width.*—4.21 mm.

Leaves (on October 14th):

*General pose.*—Outwards.

*L/B ratio.*—Medium.

*Margin.*—Generally serrate (82%), biserrate (9%), serrate-biserrate (9%).

*Size.*—Oval. Length: from 7.07 to 13.07 cm (average of 9.94 cm). Width: from 4.30 to 7.69 cm (average of 6.34 cm).

*Apex.*—Acuminate.

*Base.*—Obtuse.

*Color.*—Yellow-green group. Upper side: 147A. Under side: 148B.

*Leave blade.*—With a very strong glossiness of upper side and a medium pubescence on underside.

*Petiole.*—Length: medium; from 2.10 to 3.19 cm (average of 2.52 cm). Width measured in the middle: from 0.10 to 0.27 cm (average of 0.207 cm).

*Stipules.*—L/B ratio: much longer than broad; average length of 1.10 cm; average width of 0.19 cm.

Flowers:

*Time of beginning of flowering.*—Medium.

*Time of full flower.*—Medium-late.

*Shape.*—Moderately cupped.

*Size (diameter flower with petals pressed into horizontal positions).*—Medium.

*Petals.*—L/B ratio: longer than broad. Relation of margins: free.

*Sepal.*—Color: green with brown-red tips.

*Styles.*—Length in relation to stamens: equal. Point of fusion: away from base.

The Fruit

Dates of first and last pickings: Approximately 10 September and 8 October, respectively; depending upon the year.

Time of fruit ripening for picking: Medium-late.

Time of fruit ripening for eating: Medium-late.

Size: Medium to large fruit.

General Shape: Round. Vertical diameter of approximately 6.72 cm. Horizontal diameter of approximately 7.90 cm.

Symmetry: Asymmetric.

Ribbing: present.

*Prominence of ribbing.*—Not prominent.

Crowning at distal end: Present.

*Degree.*—Weak.

Aperture of eye: Half open.

*Size of eye.*—Large.

Sepals (visual):

*Length.*—Long.

*Pose.*—Erect convergent.

Basis: free.

Depth of eye basin: Deep 1.07 cm.

*Width of eye basin.*—Broad 3.02 cm.

*Ribbing of basin.*—Present

Degree of ribbing: Medium.

Stalk:

*Color.*—Brown/Red.

*Protrusion.*—Much beyond cavity.

*Thickness.*—Slender-medium, 2.4 mm.

*Length.*—Long, 3.44 cm.

Cavity depth of stalk: Medium, 1.27 cm.

*Width of stalk cavity.*—Medium 3.00 cm.

Skin:

*Surface texture.*—Bumpy.

*Bloom of skin.*—Absent.

Greasiness of skin: Absent.

*Cracking tendency of skin.*—Absent.

Thickness of skin: Medium.

*Shininess.*—Shiny.

Ground color of skin: Green yellow.
Over color of skin: Purple, greyed-purple group 185A/185B changing to 187B when eating ripe.
Amount of over color: Practically overall present.
*Form.*—90% solid blush with scarcely visible very fine red stripes in it; 10% striped.
Russet: Present.
*Amount of russet.*—Weak.
*Position of russet.*—Around stalk cavity.
*Color of russet.*—Buff.
*Lenticels.*—Size: medium.
*Number.*—Medium.
Flesh:
*Browning of the flesh (one hour after being cut, with stainless steel knife).*—Medium.
Firmness: Firm.
*Measurement with penetrometer.*—8.
*Color.*—Cream.
*Texture.*—Fine to medium.
*Juiciness.*—Very juicy; 70 to 75% juice.
*Acidity.*—Medium.
*Sweetness.*—Medium.
Seeds:
*Length.*—0.81 cm.
*Breadth.*—0.31 cm.
*Form.*—Acuminate.
*Color.*—Brown; brown group 200C.
Fruit in cross-section:
*Cavity beneath eye.*—V-shaped.
*Position of stamens.*—Basal.
*Shape of core.*—Symmetric.
*Distinctness of core-line (median through locules).*—Medium.
*Aperture of cells.*—Open, medium.

Other Characteristics

Use: Particularly well-suited as a dessert fruit; juices and usable for culinary purposes as well.
Keeping quality:
*Ntural conditions.*—Very good.
*Refrigerated conditions.*—Keeps very well; depending on the ripeness of the fruit, it can be stored over 12 months.
Resistance to insects and diseases: No unusual susceptibility or resistance noted.

I claim:

1. The new and distinct variety of apple tree named Jonagored Supra as described and illustrated, and which is particularly characterized over its parent variety by its rounder form of fruit; its slightly softer red-colored, approximately 90% solid blush having scarcely visible, very fine red stripes in it and approximately 10% of its surface is striped; by the earlier picking and ripening dates of its fruit; by the tree's distinctly weaker growth habit; the very dark brown to greyed-purple color of its wood; more pubescence and a lower amount of lenticels; and by the irregular margin of its leaves which is generally serrate but some also being biserrate and serrate-biserrate.

* * * * *